United States Patent [19]
Vaitekunas et al.

[11] Patent Number: 5,707,369
[45] Date of Patent: Jan. 13, 1998

[54] TEMPERATURE FEEDBACK MONITOR FOR HEMOSTATIC SURGICAL INSTRUMENT

[75] Inventors: Jeffrey J. Vaitekunas, West Chester; Geoffrey Hueil, Loveland, both of Ohio

[73] Assignee: Ethicon Endo-Surgery, Inc., Cincinnati, Ohio

[21] Appl. No.: 427,392

[22] Filed: Apr. 24, 1995

[51] Int. Cl.⁶ .................................................. A61B 17/038
[52] U.S. Cl. ....................... 606/31; 606/27; 606/32; 606/41
[58] Field of Search ......................... 606/29–31, 38, 606/40, 48–52

[56] References Cited

U.S. PATENT DOCUMENTS

| | | |
|---|---|---|
| 4,271,837 | 6/1981 | Schuler . |
| 4,474,179 | 10/1984 | Koch .................... 128/303.17 |
| 4,549,073 | 10/1985 | Tamura et al. ................ 219/497 |
| 4,685,459 | 8/1987 | Koch et al. ..................... 606/52 |
| 4,938,761 | 7/1990 | Ensslin ......................... 606/51 |
| 5,122,137 | 6/1992 | Lennox ......................... 606/40 |
| 5,147,357 | 9/1992 | Rose et al. ..................... 606/52 |
| 5,167,660 | 12/1992 | Altendorf ...................... 606/40 |
| 5,196,008 | 3/1993 | Kuenecke et al. ............... 606/35 |
| 5,207,691 | 5/1993 | Nardella ...................... 606/142 |
| 5,258,006 | 11/1993 | Rydell et al. .................... 606/52 |
| 5,342,357 | 8/1994 | Nardella ......................... 606/40 |
| 5,417,687 | 5/1995 | Nardella et al. ................. 606/32 |
| 5,422,576 | 6/1995 | Kao et al. ..................... 324/309 |
| 5,423,810 | 6/1995 | Goble et al. ..................... 606/40 |
| 5,445,635 | 8/1995 | Denen et al. ..................... 606/30 |
| 5,496,312 | 3/1996 | Klicek ......................... 606/50 |
| 5,514,129 | 5/1996 | Smith ......................... 606/40 |
| 5,540,684 | 7/1996 | Hassler, Jr. ..................... 606/51 |
| 5,558,671 | 9/1996 | Yates ......................... 606/38 |
| 5,599,350 | 2/1997 | Schulze et al. ................. 606/51 |

FOREIGN PATENT DOCUMENTS

WO 94/24949   11/1994   WIPO .
WO 94/24951   11/1994   WIPO .

OTHER PUBLICATIONS

Observations on Electrode–Tissue Interface Temperature and Effect on Electrical Impedance During Radiofrequency Ablation of Ventricular Myocardium, Brief Rapid Communications, D.E. Haines & F. Verow, Circulation vol. 82, No. 3, Sep. 1990.

*Primary Examiner*—Jennifer Bahr
*Assistant Examiner*—Bryan K. Yarnell

[57] ABSTRACT

A temperature feedback device and method is provided for the monitoring of tissue treatment status during the application of surgical heating energy. In a preferred embodiment a function of the temperature over time is used to determine when coagulation of tissue has occurred to a desired degree. Preferably an electrosurgical hemostatic energy is used to coagulate tissue. A feedback signal is provided to a user or to a controller of an electrosurgical energy source to control delivery of energy to the tissue.

20 Claims, 4 Drawing Sheets

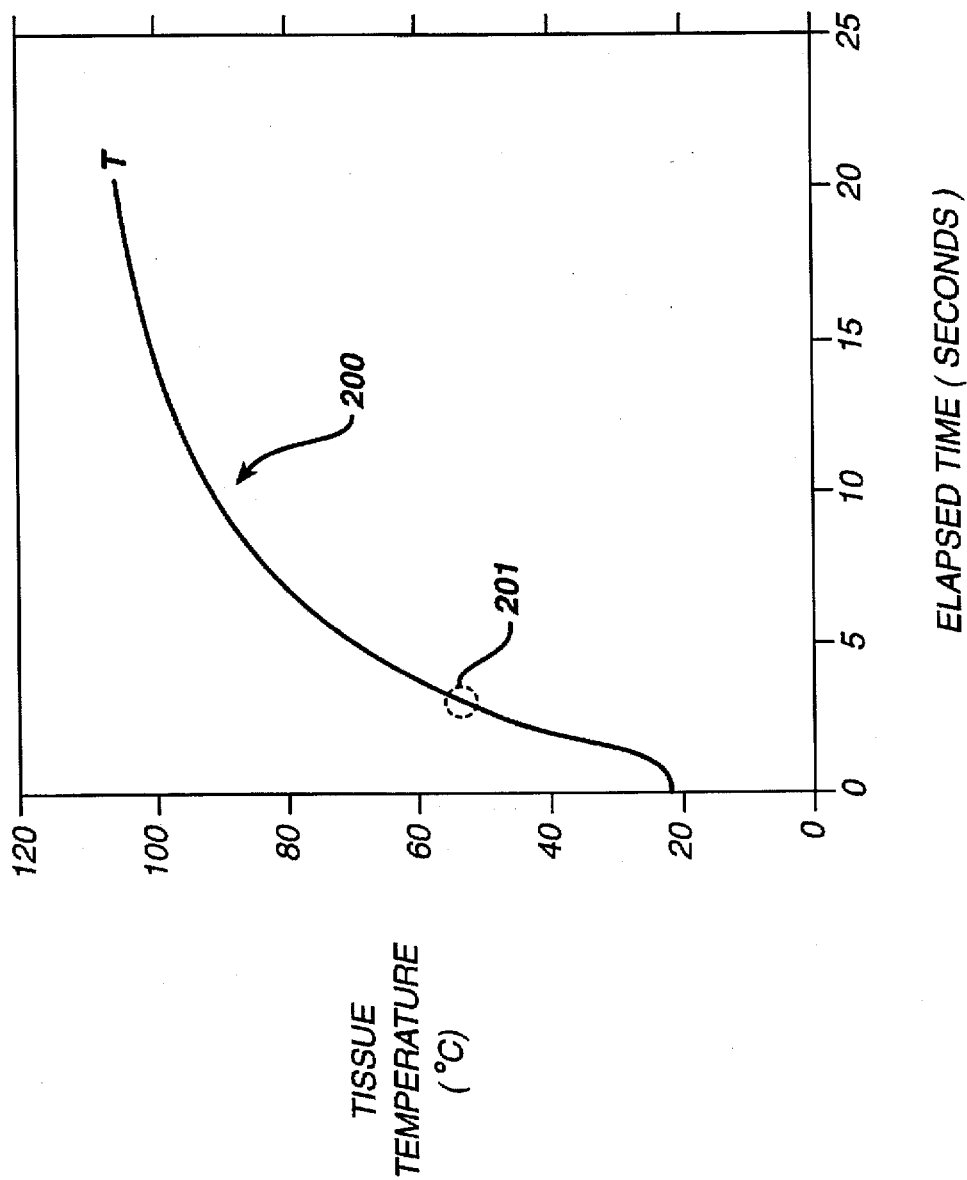

TEMPERATURE FEEDBACK MONITOR FOR HEMOSTATIC SURGICAL INSTRUMENT

FIELD OF THE INVENTION

This invention relates to a method and apparatus for controlling the heat treatment of tissue in response to the measured temperature over time as an indication of tissue treatment status of the tissue being treated by a surgical device.

BACKGROUND OF THE INVENTION

Electrosurgical hemostatic devices have been described in various instruments for cutting, cauterization, coagulation or tissue welding. Most of the devices used are either monopolar or bipolar, for example, bipolar forceps, monopolar or bipolar scissors, and cutting and coagulating devices as described in U.S. application Ser. No. 095,797, and U.S. application Ser. No. 096,154, both filed on Jul. 22, 1993 and incorporated herein by reference.

Although such instruments have been used successfully to control bleeding through the performance of surgical procedures, when such instruments are used, the primary control is the experience of the surgeon who responds to what is observed to be happening to the tissue as it is treated with the electrosurgical energy. Often, particularly for endoscopic procedures, surgeons cannot readily see what is happening to the tissue. Also, the change in tissue properties due to the electrosurgical energy may occur so quickly so as not to afford time for the surgeon to react soon enough to turn off the electrosurgical energy to the instrument. As a result, the tissue treatment may not be as precisely controlled as may be desirable. Some problems which may occur include tissue charring, sticking of the tissue to the electrodes of the surgical instrument, and over or under treatment of the tissue.

Temperature measuring devices have been described for use with electrosurgical tissue treating instruments to measure temperature and determine when the absolute temperature has exceeded a desirable temperature. These devices are typically used to signal to a user to turn off energy or to cause a control device to turn off or attenuate energy when the temperature has reached a level at which tissue sticking to the instrument may occur. Other instruments have used temperature feedback to maintain a set temperature to follow a predetermined temperature profile.

It has been recognized that tissue impedance changes as RF energy is applied to the tissue. Attempts have been made to control the power delivered to the tissue as the tissue impedance changes. For example, current has been controlled based on the change in voltage or power delivered by the generator to tissue. The differential quotient of tissue impedance as electrosurgical power is applied to the tissue has been used to determine an initial power level and to switch off electrosurgical power when the differential quotient of impedance reaches a preset value.

Notwithstanding these control arrangements, there is a continuing need for improvement in the control of heat energy delivery to the tissue and/or determination of when tissue treatment has reached an optimal level.

In particular there is a need to provide a device and method for determining the end point of coagulation using electrosurgical devices or other therapeutic heat delivering devices.

SUMMARY OF THE INVENTION

Accordingly the present invention provides a tissue monitoring device and/or method which monitors the tissue temperature at the end effector of a therapeutic tissue heating instrument as the tissue is being heated with therapeutic energy, e.g., coagulating or welding energy. Based on a model of the behavior of tissue temperature (which may be inferred from instrument temperature) over time with the delivery of therapeutic energy, the monitored tissue (or instrument) temperature is used to determine tissue treatment status.

A function of measured temperature value with respect to time is anticipated to provide the desired tissue effect. When the temperature reaches the value of the function of temperature with respect to time, i.e., the level of the temperature value for the desired results, e.g., coagulation, tissue welding, or a predetermined level of diathermy, the instrument will indicate or provide a response for such event. The indication or response may include a signal provided to an instrument user and/or a feedback mechanism arranged to control the therapeutic energy delivered to the tissue by either changing the energy delivery level or switching the energy off.

Although the present invention may be used with instruments that use various energies to heat tissue, e.g., ultrasound, microwave, laser, infrared, electrical energy, etc., a preferred embodiment provides, an electrosurgical instrument for coagulating tissue during a surgical procedure. The electrosurgical instrument preferably comprises an end effector with opposing interfacing surfaces which may be closed towards each other to engage tissue to be electrosurgically treated. Preferably the end effector includes first and second elements moveable relative to one another for engaging tissue to be coagulated therebetween. At least one of the electrical poles of the instrument is comprised of an electrode associated with at least one of the first and second elements. The electrode is in contact with tissue to be coagulated. An energy source preferably provides radiofrequency energy to the tissue contacting electrode(s) of the first and/or second elements.

A temperature sensor is located at the end effector, preferably on a first or second interfacing surface on an outer surface of one of the elements. The temperature sensor measures the temperature of the tissue engaged by the end effector either directly or indirectly. In the electrosurgical device, the temperature measuring device may be in contact with the tissue located between the first and second electrically opposite poles or may indirectly measure temperature of the tissue by measuring the temperature of the end effector. The temperature measuring device preferably comprises a temperature transducer which changes the temperature into a corresponding electrical signal reflective of the temperature at the transducer. The signal from the transducer is provided to a controlled including feedback circuitry and a device for determining a function of the temperature with respect to time.

When the function of temperature with respect to time reaches the desired level, indicating a desired tissue condition, a signal is provided to a control unit or the user, at which time the energy supply is switched off or attenuated. The feedback signal may, for example, provide a visual audible or tactile signal to a user, and/or may provide instructions to a control unit to automatically turn off energy supply to the tissue.

The energy source may be responsive to a power control signal of a controller. The feedback circuitry may be coupled to or included with the power controller which may include at least one electrical switch for selectively controlling the electrosurgical energy supplied to the instrument to coagulate tissue positioned between the first and second elements.

The power controller may selectively switch off power supply to the tissue under a number of therapeutic tissue conditions such as e.g. coagulation complete.

Some indicators which may be used to determine achievement of desired tissue status may include, e.g. reaching the point of inflection or critical point of temperature with respect to time, or a ratio or percentage above the point of inflection or critical point.

Although this instrument may be a monopolar device or a multipolar device including two or more than two poles, the end effector preferably includes two electrically opposite electrodes corresponding to two electrically opposite poles.

One embodiment includes a cutting element associated with the end effector. The cutting element is arranged to cut tissue at or near the coagulation site. Preferably once the temperature monitor determines that tissue is coagulated or cauterized, the cutting element is then used to cut through the coagulated tissue or between two zones of tissue coagulation.

In another embodiment the hemostatic device is incorporated into a linear cutter similar to a linear cutting mechanical stapler. In this embodiment the hemostatic device comprises two substantially parallel and elongated bar electrodes which are associated with one pole of an electrosurgical system, and a slot for a cutting means to travel between the bars. Optionally, one or more rows of staples may be provided on each side of the slot and bars to provide additional hemostasis. Of course other end effector configurations are contemplated by this invention. For example, the device may be a circular anastomosis cutting and coagulating device.

In accordance with another aspect of the present invention a method of operating an apparatus for surgically heat treating tissue during surgical procedure is provided. Accordingly a preferred method comprises the steps of: engaging tissue to be surgically treated with the end effector of a surgical instrument; applying therapeutic tissue heating energy to the tissue to be treated; measuring the temperature of the tissue as it is being treated; generating a signal representative of the temperature of the tissue; and controlling the therapeutic tissue heating energy applied to the electrosurgical instrument in response to the temperature signal.

The step of controlling the therapeutic tissue heating energy applied to the electrosurgical instrument may comprise the steps of determining a function of temperature with respect to time; comparing the calculated function of temperature with respect to time to a threshold value for the function of temperature; and generating a control signal to control or switch off the power of the controller upon the condition of the calculated function of temperature with respect to time reaching the threshold function of temperature.

In a preferred embodiment the function of temperature with respect to time is the second derivative of the temperature with respect to time and the threshold value of the function of temperature is zero. Alternatively other functions of the temperature with respect to time may be used. For example, the first derivative may be used, percentages above the first or second derivative may be used, or specific values may be sampled at specific times during the application of electrosurgical energy.

In another preferred embodiment of the step of applying therapeutic tissue heating energy comprises applying electrosurgical energy to tissue.

These and other objects and advantages of the invention will be apparent from the following description, the accompanied drawings and the following claims.

DESCRIPTION OF THE DRAWINGS

FIG. 4 illustrates a characteristic curve of temperature versus time of tissue being treated with the electrosurgical forceps illustrated in FIG. 1.

DETAILED DESCRIPTION OF THE DRAWINGS

While the present invention is generally applicable to a variety of electrosurgical instruments including monopolar, bipolar and multipolar instruments (i.e., including two or more therapeutic electrodes providing energy in waveforms as measured from any pole to any other pole as having a phasic relationship), cutting instruments, instruments with mechanical tissue fastening, and both conventional and endoscopic type instruments, it will be described herein with reference to an endoscopic bipolar forceps instrument.

Figure 1:
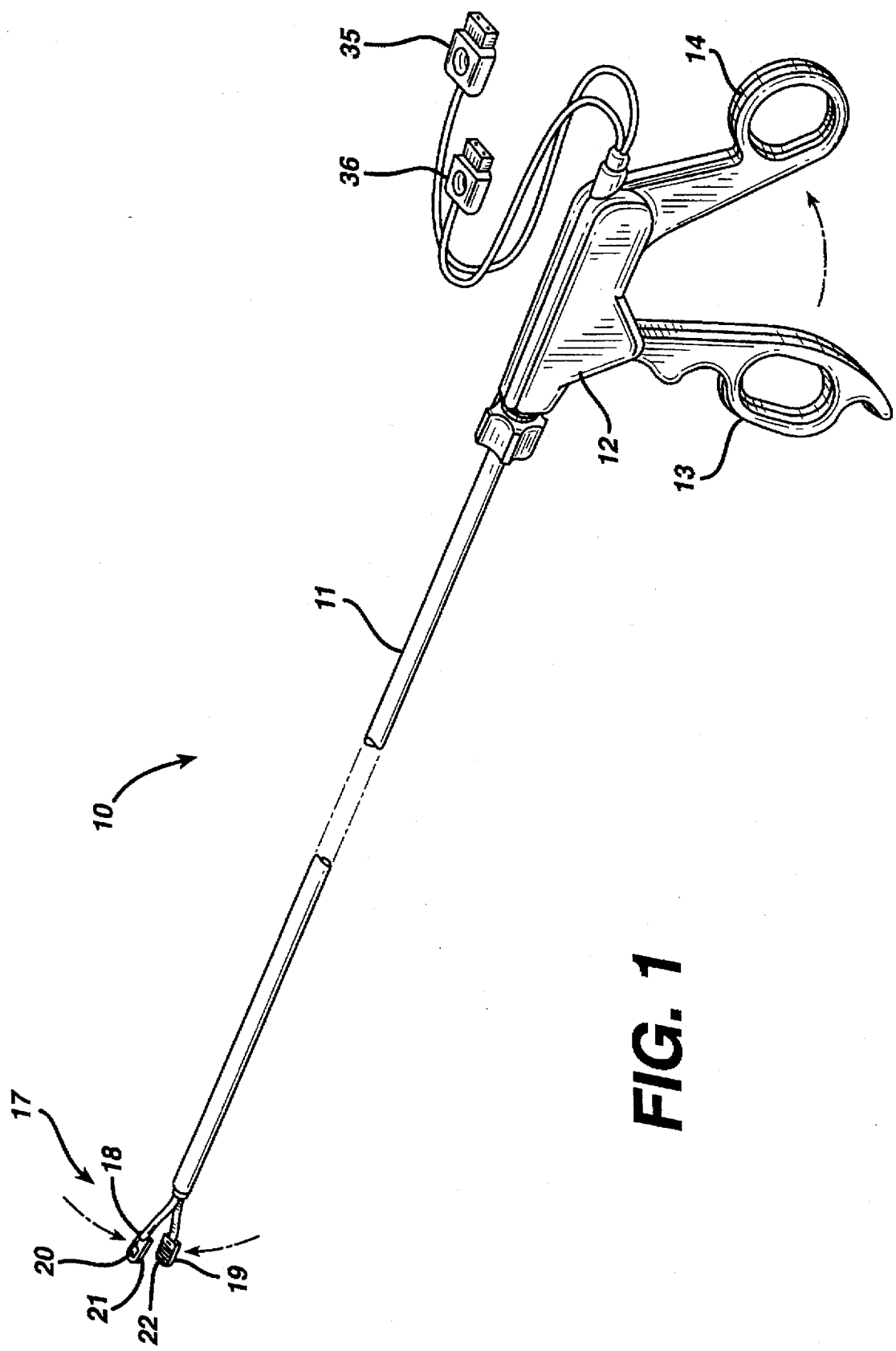
FIG. 1 is a perspective view of an electrosurgical instrument with a temperature feedback device of the present invention.
Figure 2:
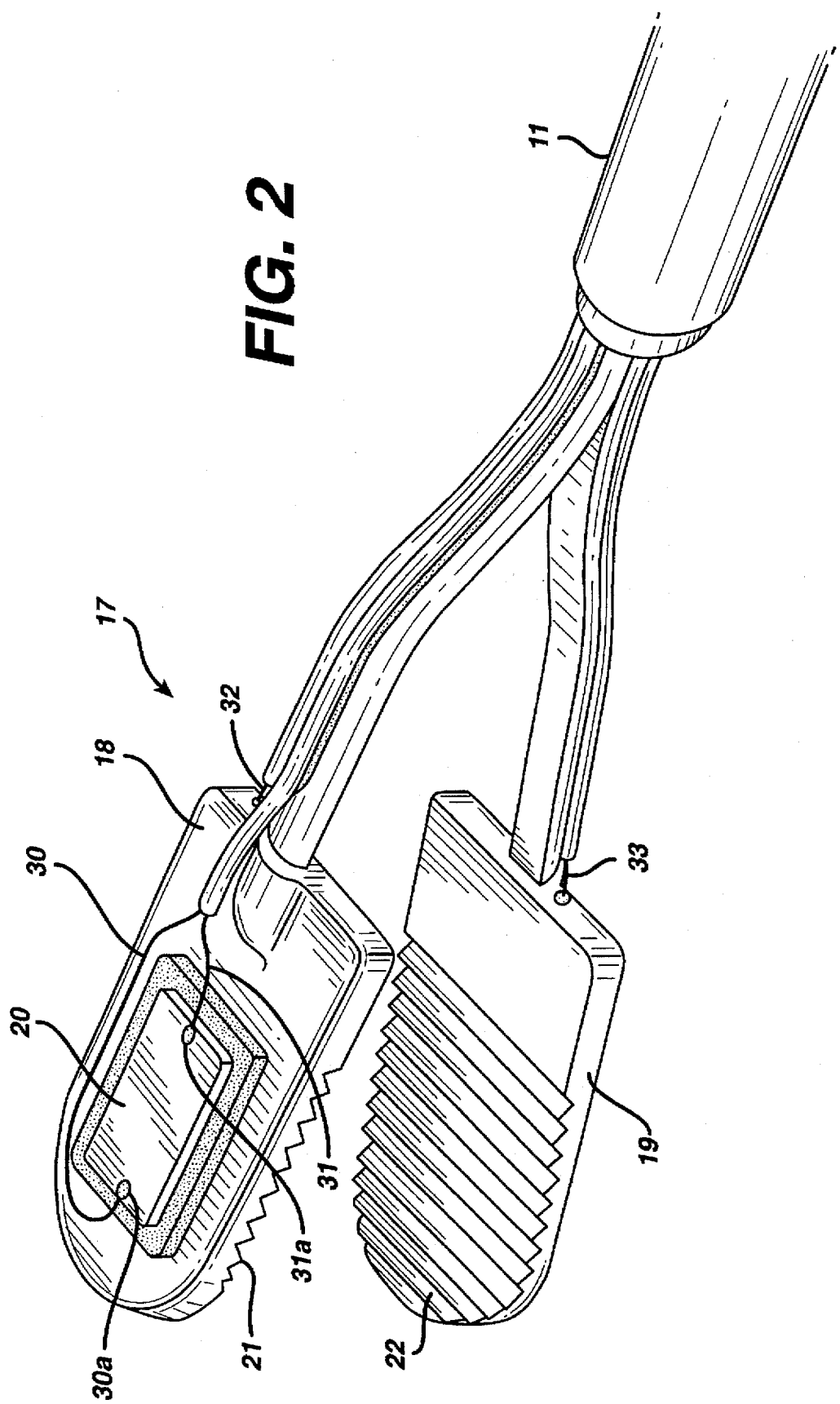
FIG. 2 is a perspective view of the distal end of the instrument of FIG. 1.
Figure 3:
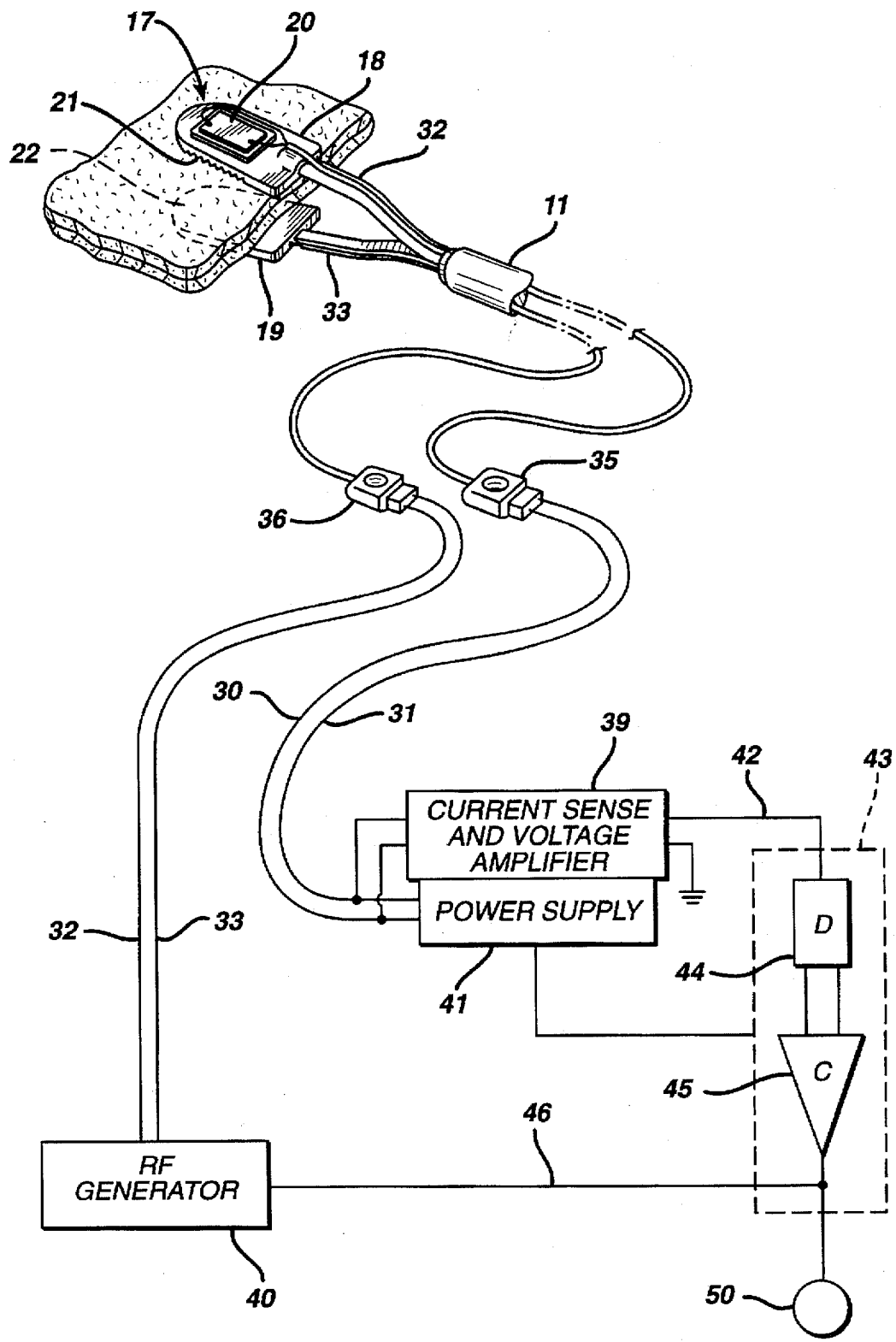
FIG. 3 is a partial perspective, partial schematic illustration of the temperature feedback device of FIG. 1.

Referring to FIGS. 1-3 there is illustrated a bipolar forceps instrument 10 having a temperature feedback device of the present invention. The instrument 10 includes a handle portion 12 including actuating members 13, 14 for actuating the tissue grasping elements 18, 19 of the forceps distal end. The handle portion 12 is coupled to a closure tube 11 extending to the distal end 17 of the instrument 10. The grasping elements 18, 19 at the distal end 17 of the instrument are movable relative to each other for engaging tissue to be coagulated therebetween. The instrument 10 is operated in a conventional well known manner by moving the actuating element 13 toward actuating element 14 to advance closure tube 11 to close grasping elements 18, 19 towards each other. Accordingly, description of the forceps will be made only to the extent necessary for understanding the present invention.

Grasping elements 18, 19 include a tissue contacting interfacing surfaces 21, 22, respectively. Grasping elements 18, 19 are electrically isolated from each other and at least a portion of the surfaces 21, 22 are formed of an electrically conductive material arranged to conduct electrically opposite bipolar energy through tissue engaged between the surfaces 18, 19. Conductors 32, 33 are in electrical contact with electrically conductive tissue treating portions of surfaces 21, 22 respectively, and extend through tube 11 into handle portion 12 and through connector 36 to generator 40.

Grasping element 18 includes a temperature sensor 20 secured to the outer back surface of the element 18. The temperature sensor 20 is preferably a resistance thermal device (R.T.D.) that is epoxied to the outer surface of grasping element 18. The temperature sensor 20 is coupled to conductors 30, 31 by way of contacts 30a, 31a located at opposite ends of the sensor 20. An electrical energy supply 41 supplies a DC voltage to the sensor through conductors 30, 31. The conductors 30, 31 terminate in a connector 35 which couples the energy source 41 and temperature monitoring circuitry to the conductors 30, 31. The conductors 30, 31 are electrically isolated from each other and extend through the shaft 11 and handle portion 12 terminating in connector 35.

Conductors 30, 31 are also coupled to a voltage and current sensing device 39. The device 39 includes current and voltage sensing means arranged to sense the current and voltage of the circuit including the RTD temperature sensor 20 and conductors 30, 31. Such sensing means are known in the art and typically include voltage and current transformers. The sensing device 39 includes a divider which divides the voltage by current to provide a signal representative of the resistance of the RTD sensor 20.

The signal representative of resistance is amplified by an amplifier included with the sensing device RTD 39. The output of the voltage and current sensing device 39 is coupled to a controller 43 and communicates the representative signal to include a double differentiator 44 included with the controller 43. The controller 43 may also include other control circuitry, e.g., a microprocessor for controlling various functions such as generator control. The differentiator 44 is arranged to determine the point of inflection of the signal at output 42 of the sensing device 39. The output of the differentiator 44 is coupled to a comparitor 45 which provides a signal to the generator 40 when the value at the output of the differentiator 44 reflects a point of inflection equal to zero. The output 46 of the comparator 45 is input into the generator 40 to turn off energy supplied to the forceps grasping elements 18, 19 when the second derivative is equal to zero. Devices or circuits capable of performing this task are known in the art. A reset switch 50 such as a foot controlled switch 50 or a button is coupled to the controller 43. The foot switch 50 or reset button causes the controller 43 to provide a reset signal to the generator 40. The generator 40 must then receive a signal from the controller 43 to reset the generator 40 to apply electrosurgical energy.

In operation the forceps are used to coagulate tissue to a desired degree and/or to weld layers of tissue together. Generally tissue welding is defined to mean bringing two pieces of tissue together and joining them. The welding operation is believed to be performed by causing collagen molecules in the tissue to be mobilized by severing the disulfide cross linkages. The collagen molecules then fuse across the interface between the two pieces of tissue. Finally, new disulfide linkages are believed to form across the interface between the two pieces of tissue, thereby causing the interface to disappear. In use, the function of temperature with respect to time is used to determine when the desired results e.g. coagulation or tissue welding, occurs.

Referring now to FIG. 4 a characteristic curve 200 of temperature vs. time using the bipolar forceps of FIGS. 1–3 is shown. The curve represents the temperature of pig's liver tissue with an average power delivery during the course of treatment of 125 watts. At point 201 on curve 200, the point of inflection or the second derivative of temperature, $dT/d_t^2 = 0$. This point 201 is selected to be the threshold function of temperature, $f(T)_{thresh}$, at which coagulation is complete.

The feedback system is designed to indicate when a desired or predetermined tissue effect has occurred. In this particular embodiment the desired tissue effect is coagulation complete. An audible, visible, tactile or other feedback system may be used to indicate when sufficient cauterization has occurred according to the threshold value as illustrated in FIG. 4. At this point, the RF energy may be turned off.

In operation the instrument 10 is placed through an access tube such as a cannula of a trocar obturator. The grasping surfaces 18, 19 of the forceps are spread apart by moving the actuating element 13 away from the actuating element 14. Tissue is placed between the tissue contacting surfaces 21, 22 of grasping elements 18, 19 respectively. The grasping elements 18, 19 then are closed onto the tissue by moving the handle element 13 towards handle element 14 advancing the tube 11 over the grasping elements 18, 19 to close them.

Once the tissue is appropriately placed and engaged between the grasping members 18, 19, the electrosurgical energy may be applied to the tissue through the tissue contacting surfaces 21, 22 by activating a switch such as foot pedal switch 50. The foot pedal switch 50 sends a signal to the controller 43 which then provides a signal to the RF generator 40 to deliver RF energy to grasping elements 18, 19. The grasping elements 18, 19 deliver electrosurgical energy through the engaged tissue through tissue contacting surfaces 21, 22.

The switch 50 also activates the temperature sensor 20 by signaling to energy source 41 to supply temperature sensing DC low voltage to the temperature sensor 20. The electrical signal is coupled from conductors 30, 31 of the temperature sensor 20 to the current and voltage sensing device 39. The voltage across and current flowing through the temperature 20 sensor is sensed and used to determine the impedance of the sensor 20 which is proportional to the temperature of the grasping element 18. The temperature of the grasping element 18 is proportional to the temperature of the tissue engaged between the grasping element 18 and the grasping element 19.

The controller 43 includes the differentiator 44 which determines the second derivative of the temperature and outputs a corresponding signal to a comparitor 45. The comparitor 45 changes state when the second derivative is equal to zero. The output 46 of the comparitor 45 is coupled to the RF generator 40. The output signal from the comparitor 45 to the RF generator tells the generator to turn off the RF energy delivered to the grasping elements 18, 19, when the second derivative is equal to zero. The controller 43 may also provide a corresponding signal to the user to inform the user that the temperature sensor has detected a coagulation complete condition, Some variations of this invention have been described in connection with specific embodiments involving endoscopic bipolar forceps and endoscopic stapling and cutting devices. Naturally, the invention may be used in numerous applications where electrosurgical energy or other tissue heating energies are used to treat tissue such as ultrasound, microwave, laser and infrared energy. Accordingly is will be understood by those skilled in the art that various changes and modifications may be made in the invention without departing from its scope, which is defined by the following claims and their equivalents.

I claim:

1. A therapeutic tissue heating instrument comprising:
   a shaft having a distal end;
   an end effector located at the distal end of the shaft, said end effector comprising:
   a tissue contacting surface, at least a portion of said tissue contacting surface being energy conductive to heat tissue in contact with said energy conductive portion;
   a temperature measuring device arranged to measure the temperature of tissue being treated by said energy conductive portion and to produce a temperature signal representative of the measured temperature;
   a signal processing device coupled to said temperature measuring device, said signal processing device arranged to receive the temperature signal over a period of time;
   said signal processing device comprising a function calculating device arranged to calculate a function of tissue temperature over time from the temperature signal provided to said signal processing device during the period of time;

a comparison device coupled to the function calculating device, said comparison device arranged to compare the function of tissue temperature over time to a threshold function value to provide a tissue status signal in response thereto wherein the function of tissue temperature with respect to time is a second derivative of the tissue temperature with respect to time.

2. The instrument of claim 1 wherein the threshold function value is about zero.

3. The instrument of claim 1 wherein said end effector comprises:

first and second elements comprising first and second opposed tissue contacting surfaces respectively, said surfaces moveable relative to each other from an open, spaced-apart position for positioning tissue therebetween to a closed position for approximating the time, wherein said energy conductive portion is formed on at least one of said first and second surfaces.

4. The instrument of claim 1 wherein said period of time comprises a plurality of time intervals and wherein said function calculating device is arranged to calculate the function of tissue temperatures over time at the plurality of time intervals.

5. An electrosurgical instrument comprising:

a shaft having a distal end;

an end effector located at the distal end of the shaft, said end effector comprising:

a tissue contacting surface, at least a portion of said tissue contacting surface being electrically conductive to treat tissue in contact with said electrically conductive portion;

a temperature measuring device arranged to measure the temperature of tissue being treated by said electrically conductive portion and to produce a temperature signal representative of the measured temperature;

a signal processing device coupled to said temperature measuring device, said signal processing device arranged to receive the temperature signal over a period of time;

said signal processing device comprising a function calculating device arranged to calculate a function of tissue temperature over time from the temperature signal provided to said signal processing device during the period of time;

a comparison device coupled to the function calculating device, said comparison device arranged to compare the function of tissue temperature over time to a threshold function value to provide a tissue status signal in response thereto wherein the function of tissue temperature with respect to time is a second derivative of the tissue temperature with respect to time.

6. The electrosurgical instrument of claim 5 wherein the threshold function value is about zero.

7. The electrosurgical instrument of claim 5 wherein said end effector comprises:

first and second elements comprising first and second opposed tissue contacting surfaces respectively, said surfaces moveable relative to each other from an open, spaced-apart position for positioning tissue therebetween to a closed position for approximating the tissue, wherein said electrically conductive portion is formed on at least one of said first and second surfaces.

8. The electrosurgical instrument of claim 5 wherein said period of time comprising a plurality of time intervals and wherein said function calculating device is arranged to calculate the function of tissue temperatures over time at the plurality of time intervals.

9. A method for surgically treating tissue comprising:

providing an surgical instrument comprising:

a shaft having a distal end;

an end effector located on the distal end of the shaft, said end effector comprising a tissue engaging portion and an energy delivering device associated with the tissue engaging portion, and said end effector adapted to transmit heat causing energy to tissue engaged by said end effector;

a temperature measuring device arranged on said end effector to measure the temperature of tissue being treated by said end effector and to produce a temperature signal representative of the measured temperature;

a signal processing device coupled to said temperature measuring device; and an energy source coupled to the energy delivering device of the end effector;

contacting tissue to be treated with said tissue contacting surface;

delivering energy from said source to the tissue;

measuring the temperature with said temperature measuring device and generating a temperature signal representative thereof;

communicating the temperature signal to the signal processing device;

calculating a function of the temperature with respect to time wherein said function of tissue temperature with respect to time is a second derivative of the tissue temperature with respect to time;

making a comparison between the calculated function of temperature and a function threshold value; and generating a feedback signal in response to the comparison, said feedback signal indicating status of tissue treatment.

10. The surgical method of claim 9 wherein said feedback signal comprises a perceivable signal to the user.

11. The surgical method of claim 10 wherein said signal indicates whether or not tissue coagulation is complete.

12. The surgical method of claim 9 wherein said feedback signal comprises a control signal and wherein said energy source is responsive to said control signal.

13. The surgical method of claim 12 wherein said control signal turns off the delivery of the heat causing energy delivered by the energy source to the end effector to be terminated, upon a condition of said control signal indicating completion of tissue treatment.

14. The surgical method of claim 13 wherein the control signal turns off the heat causing energy when tissue coagulation is completed to a desired degree.

15. A method for electrosurgically treating tissue comprising:

providing an electrosurgical instrument comprising:

a shaft having a distal end;

an end effector located on the distal end of the shaft, said end effector comprising:

a tissue contacting surface, at least a portion of said surface being electrically conductive, said end effector adapted to receive electrosurgical energy and to conduct the electrosurgical energy through said electrically conductive portion of said surface to treat tissue in contact therewith;

a temperature measuring device arranged to measure the temperature of tissue being treated by said end effector and to produce a temperature signal representative of the measured temperature;

a signal processing device coupled to said temperature measuring device;

an electrosurgical energy source coupled to the electrically conductive portion of the end effector;

contacting tissue to be treated with said tissue contacting surface;

delivering electrosurgical energy from said source to the tissue;

measuring the temperature with said temperature measuring device and generating a temperature signal representative thereof;

communicating the temperature signal to the signal processing device;

calculating a function of the temperature with respect to time wherein the step of calculating a function of tissue temperature with respect to time comprises calculating a second derivative of the tissue temperature with respect to time;

making a comparison between the calculated function of temperature and a function threshold value; and generating a feedback signal in response to the comparison, said feedback signal indicating status of tissue treatment.

16. The electrosurgical method of claim 15 wherein said feedback signal comprises a perceivable signal to a user.

17. The electrosurgical method of claim 16 wherein said signal indicates whether or not tissue coagulation is complete.

18. The electrosurgical method of claim 16 wherein said feedback signal comprises a control signal and wherein said energy source is responsive to said control signal.

19. The electrosurgical method of claim 18 wherein said control signal turns off the delivery of electrosurgical energy delivered by the energy source to the end effector, upon a condition of said control signal indicating completion of tissue treatment.

20. The electrosurgical method of claim 19 wherein the control signal turns off electrosurgical energy when tissue coagulation is completed to a desired degree.

* * * * *